United States Patent [19]

Bajusz et al.

[11] Patent Number: 4,465,625
[45] Date of Patent: Aug. 14, 1984

[54] PENTAPEPTIDES AND PROCESS FOR THEIR PREPARATION

[75] Inventors: Sándor Bajusz; András Rónai; József Székely; László Gráf; Zsuzsa Mohai née Nagy, all of Budapest, Hungary

[73] Assignee: Richter Gedeon Vegyeszeti Gyar, Budapest, Hungary

[21] Appl. No.: 830,831

[22] Filed: Sep. 6, 1977

[30] Foreign Application Priority Data

Sep. 16, 1976 [HU] Hungary .................. GO 1350

[51] Int. Cl.³ .......................................... C07C 103/52
[52] U.S. Cl. .............................................. 260/112.5 E
[58] Field of Search ................................. 260/112.5 E

[56] References Cited

PUBLICATIONS

"Progress in Medicinal Chemistry", vol. 17, p. 22, Elsevier North-Holland, Amsterdam, New York, Oxford (1980).

Annual Review of Pharmacology and Toxicology, 20, 81–110, Morley (1980).

British Journal Pharmacology 68, 333–343, Kosterlitz et al. (1980).

"Synthetic Enkephalin Analogues in Hormonally Active Brain Peptides", Bajusz et al. (1982).

Primary Examiner—Delbert R. Phillips
Attorney, Agent, or Firm—Karl F. Ross; Herbert Dubno

[57] ABSTRACT

Analgesic compounds having the formula (I):

Tyr-A-Gly-Phe-B-X-Y wherein

A is a D-aminoacid group having a lower alkyl group or a lower thioalkyl group as a side chain, B is an aminoacid or a cyclic iminoacid group, either of which has a lower alkyl group as a side chain, X is an oxygen atom or an NH group, and Y is a hydrogen atom or a lower alkyl group, or a pharmaceutically effective amide, ester or salt thereof.

1 Claim, No Drawings

PENTAPEPTIDES AND PROCESS FOR THEIR PREPARATION

The invention relates to novel pentapeptides having the general formula I

Tyr-A-Gly-Phe-B-X-Y    (I)

wherein
- A stands for a D-aminoacid group having a lower alkyl group or a lower thioalkyl group as a side chain,
- B stands for an aminoacid or a cyclic iminoacid group, both having a lower alkyl group as a side chain,
- X stands for an oxygen atom or an NH group, and
- Y stands for a hydrogen atom or a lower alkyl group and their derivatives and salts. Furthermore the invention relates to a process for the preparation of these compounds.

The abbreviations applied in the present specification for the denomination of aminoacids, peptides, their derivatives and their substituents, furthermore for the denomination of the location of the aminoacids present in the peptides comply with the recommendations of the IUPAC-IUB Commission on Biochemical Nomenclature (Biochemistry 5, 2485 (1966); 6, 322 (1967); J. Biol. Chem. 241, 2491 (1966); 242, 555 (1967); 247, 977 (1972).

The three-letter abbreviations of aminoacids are as follows:

| | |
|---|---|
| Ala = alanine | Met = methionine |
| Gly = glycine | Phe = phenylalanine |
| Ile = isoleucine | Pro = proline |
| Leu = leucine | Tyr = tyrosine |
| Nle = norleucine = 2-aminohexanic acid. | |

The abbreviation itself denotes the aminoacid in an L-configuration (with the exception of the inactive Gly) whereas a D-aminoacid is denoted in each e.g. D-Met=D-methionine.

A hyphen standing before or after the abbreviation indicates that a hydrogen atom is missing from the α-amino or -imino-group or a hydroxyl group is missing from the α-carbonyl group. Consequently, alanine=Ala=H-Ala-OH; carbobenzoxyalanine=Z-Ala because Z=carbobenzoxy, and alanine methylester=Ala-OMe because Me=methyl.

It follows from the applied system of abbreviations that both Gly-Phe-Nle and H-Gly-Phe-Nle-OH denote glycyl-L-phenylalanyl-L-norleucine. The aminoacid components are numbered on beginning at the amino-terminal. Thus, the intermediate Gly-part of the tripeptide Tyr-Gly-Gly is Gly$^2$ whereas its Gly-part on the carboxy terminal is Gly$^3$.

In addition to these also the following abbreviations are used:
- Z=benzyloxycarbonyl=carbobenzoxy
- Boc=tert.butyloxycarbonyl
- OTCP=2,4,5-trichlorophenoxy
- OPCP=pentachlorophenoxy
- ONP=4-nitrophenoxy
- Et=ethyl.

It is known that natural Met-enkephalin of the formula II

Tyr-Gly-Gly-Phe-Met-OH    (II)

and Leu-enkephalin of the formula III

Tyr-Gly-Gly-Phe-Leu-OH    (III), of which the pentapeptide of the formula II corresponds to the fragment 61–65 of β-lipotropin, possess a morphine-like effect (J. Hughes et al.: Nature 258, 577 (1975). This morphine-like effect of the compounds of the formula II and III manifests itself in the way that they are bound in vitro to opiat receptors. However, their activity in vivo is disputable. An analgesic effect characteristic of morphine could be unambiguously detected only in case of β-lipotropin fragments having a higher number of members such as the fragments 61–67 and 61–91 (L. Gráf et al.: Nature (1976), under publication). Up to the present no pentapeptide derivatives or analogue could be prepared whose in vitro activity would have exceeded that of Met-enkephalin or even that of the less active Leu-enkephalin (L. Terenius et al.: Biochem. Biophys. Res. Commun. 71, 175 (1976), or whose analgesic effect could have been unequivocally proved.

The invention aims at preparing novel pentapeptides and pentapeptide derivatives whose morphine-like activity manifests itself also in vivo.

Now it has been found that on modifying the molecule of enkephalins of the formula II and III, on substituting the aminoacid groups Gly$^2$ and Leu$^5$ or Met$^5$, pentapeptides and pentapeptide derivatives having an analgesic effect commensurable with that of morphine can be prepared. It has proved to be favorable to insert, instead of the Gly$^2$ group, a D-aminoacid group having a lower alkyl or lower thioalkyl group as a side chain, and to substitute for the Leu$^5$ or Met$^5$ part, respectively, an aminoacid group or a cyclic iminoacid group, both having a lower alkyl group as a side chain, or an ester or amide derivative thereof.

Accordingly, the invention relates to a process for the preparation of pentapeptides and pentapeptide derivatives having the formula I, wherein A, B, X and Y have the same meanings as above, furthermore of their salts, said process comprising the steps of condensing an aminoacid having a lower alkyl group as a side chain or a cyclic iminoacid having a lower alkyl group as a side chain, or an ester or amide derivative of any of these aminoacids in a way known in the peptide chemistry, with the consecutively following aminoacids and/or peptide fragments having a protecting group which can be split off at the amino-terminal, and, if desired, converting the peptide intermediate protected on its amino-terminal into an ester or amide derivative, and, if desired, subsequent to the removal of the protecting group, forming a salt with an acid.

The in vivo observed morphine-like effect of the compounds of the formula I referred to that of Met-enkephalin and of morphine is shown in Table I. The activity of morphine was considered to be 100.

The investigations were carried out with the method of D'Amour and Smith (J. Pharm. Ther. 72, 74 (1941)) and, resp., of Chermat and Simon (J. Pharmacol. (Paris) 6, 489 (1975).

It appears from the results of these investigations that, in contrast to Met-enkephalin of the formula II, the morphine-like effect of the compounds of the formula I manifests itself also in vivo, and several of these compounds show activities exceeding even that of morphine which served as a reference substance.

TABLE I

Morphine-like effect of compounds of the general formula I

| No. of the Example | Compound Tyr—A—Gly—Phe—B—X—Y (I) —A— | —B—X—Y | Activity in vivo |
|---|---|---|---|
| 1 | —D-Ala— | —Nle—O—H | 2 |
| 2 | —D-Ala— | —Nle—O—Me | 2 |
| 3 | —D-Met— | —Nle—O—H | 2 |
| 4 | —D-Ala— | —Ile—O—H | 2 |
| 5 | —D-Ala— | —Pro—O—H | 24 |
| 8 | —D-Nle— | —Pro—O—H | 100 |
| 7 | —D-Met— | —Pro—O—H | 133 |
| 11 | —D-Ala— | —Pro—NH—H | 390 |
| 6 | —D-Ala— | —Pro—NH—Et | 1690 |
| 9 | —D-Met— | —Pro—NH—Et | 1690 |
| 10 | —D-Met— | —Pro—NH—H | 5000 |
| Reference substance: | Tyr—Gly—Gly—Phe—Met—OH (II) | | 0 |
| Reference substance: | morphine | | 100 |

The process according to the invention is further illustrated by the following Examples which are given for the purposes of illustration and are not to be construed as limiting in any respect the scope of protection.

In the Examples, temperature values are given in Centigrade (°C.). The $R_f$ values were determined by thin layer chromatography on silica gel (Kieselgel G, Reanal, Budapest) in the following solvent mixtures:
1. chloroform-methanol (9:1)
2. ethyl acetate-pyridine-acetic acid-water (240:20:6:11)
3. ethyl acetate-pyridine-acetic acid-water (120:20:6:11)
4. ethyl acetate-pyridine-acetic acid-water (60:20:6:11)
5. ethyl acetate-pyridine-acetic acid-water (30:20:6:11).

The solutions were evaporated at a reduced pressure on a water bath of 40° C. The aminoacid analysis of the peptides was carried out by an analyzer of JLC-5AN type, after complete hydrolysis (6N HCl, 24 hours, 110°).

EXAMPLE 1

Preparation of L-tyrosyl-D-alanyl-glycyl-L-phenylalanyl-L-norleucine

1st step: Benzyloxycarbonyl-L-phenylalanyl-L-norleucine methylester 4.8 g. (10 mmoles) of Z-Phe-OTCP (J. Pless and R. A. Boissonas: Helv. Chim. Acta 46, 1609 (1963) and 2 g. (11 mmoles) of H-Nle-Ome.HCl (H. M. Flowers and W. S. Reith: Biochem. J. 53, 657 (1953)) are dissolved in 10 ml. of pyridine, then 1.2 ml. (11 mmoles) of N-methylmorpholine added and allowed to stand for 3 hours. On evaporating the reaction mixture, the residue is dissolved in 50 ml. of a 1:1 mixture of ethyl acetate and water, the organic phase washed with 1N hydrochloric acid and water, then dried on sodium sulphate and evaporated. The residue is rubbed with ether, filtered, washed with ether and dried. Yield: 3.6 g. (85%) of the named product; m.p. 123°-124°; $R_f^1$ 0.89-0.93.

2nd step: Benzyloxycarbonyl-glycyl-L-phenylalanyl-L-norleucine methylester 5.55 g. (13 mmoles) of Z-Phe-Nle-OMe (1st step of Example 1) are dissolved in 100 ml. of methanol and hydrogenated in the presence of palladium catalyst. At the end of the reaction ($R_f^2$ 0.23-0.25) the catalyst is filtered off, the solution is evaporated and the residue is dissolved in 25 ml. of pyridine. On adding 4.66 g. (12 mmoles) of Z-Gly-OTCP (J. Pless and R. A. Boissonas: Helv. Chim. Acta 46, 1609 (1963)) the mixture is allowed to stand for 3 hours. The reaction mixture is evaporated, the residue rubbed with ether, filtered, washed with ether and dried. Yield: 5.28 g. (91%) of named product; m.p. 110°-112°; $R_1^1$ 0.80-0.90.

3rd step: Benzyloxycarbonyl-L-tyrosyl-D-alanyl-glycyl-L-phenylalanyl-L-norleucine methylester 1.93 g. (4 mmoles) of Z-Gly-Phe-Nle-OMe (2nd step of Example 1) are dissolved in 30 ml. of methanol and hydrogenated in the presence of palladium catalyst. At the end of the reaction ($R_f^2$ 0.10-0.20) the catalyst is filtered off, the solution is evaporated and the residue is dissolved in 8 ml. of pyridine. On adding 1.6 g. (4 mmoles) of Z-D-Ala-OTCP (whose synthesis is identical with that of the L-isomer: J. Pless and R. A. Boissonas: Helv. Chim. Acta 46, 1609 (1963)) the mixture is allowed to stand for 3 hours. The reaction mixture is evaporated, the residue rubbed with ether, filtered, washed with ether and dried. The product obtained in this way ($R_f^2$ 0.67-0.70) is dissolved in 50 ml. of a 1:1:1 mixture of methanol-water-dimethyl formamide and hydrogenated in the presence of palladium catalyst. At the end of the reaction ($R_f^2$ 0.24-0.29) the catalyst is filtered off, the solution evaporated and the residue dissolved in 8 ml. of pyridine. On adding 1.75 g. (3.5 mmoles) of Z-Tyr-OTCP (J. Pless and R. A. Boissonas: Helv. Chim. Acta 46, 1609 (1963)) the mixture is allowed to stand for 5 hours. The reaction mixture is evaporated, the residue dissolved in 30 ml. of ethyl acetate, washed with water, dried on sodium sulphate and evaporated. The residue is rubbed with a 1:1 mixture of ether and n-heptane, filtered, washed with the same 1:1 mixture and dried. Yield: 2.0 g. (80%) of the named product; m.p. 195° (shrinks at 190°); $R_f^3$ 0.73-0.78.

4th step: L-Tyrosyl-D-alanyl-glycyl-L-phenylalanyl-L-norleucine 1.15 g. (1.6 mmoles) of Z-Tyr-D-Ala-Gly-Phe-Nle-OMe (3rd step of Example 1) are suspended in a mixture of 4 ml. of methanol and 2 ml. of acetone, then saponified with 0.5N sodium hydroxide in the presence of thymolphthalein as indicator. When the alkali consumption becomes slower, the mixture is diluted with 10 ml. of water and shaken with 3×5 ml. of ethyl acetate. On evaporating the ethyl acetate phases 0.3 g. (26%) of protected pentapeptide ester is recovered. The aqueous phase is acidified with 0.5N sulphuric acid, the precipitated substance ($R_f^2$ 0.25-0.35) suspended in 50 ml. of 80% acetic acid and hydrogenated in the presence of palladium catalyst. In the course of the reaction the substance is dissolved. At the end of the reaction the catalyst is filtered off, the solution evaporated and the residue rubbed with about 4 ml. of cold water. The formed crystalline substance is filtered, washed with cold water and dried. Yield: 0.47 g. (70%) of the named product; $R_f^4$ 0.19-0.23. Aminoacid analysis: Gly=1.0, Ala=1.02; Nle=1.02; Tyr=0.98; Phe=1 (reference basis).

EXAMPLE 2

Preparation of
L-tyrosyl-D-alanyl-glycyl-L-phenylalanyl-L-norleucine methylester hydrochloride 0.36 g. (0.5 mmoles) of Z-Tyr-D-Ala-Gly-Phe-Nle-OMe (3rd step of Example 1) are suspended in 30 ml. of 80% acetic acid and hydrogenated in the presence of palladium catalyst. At the end of the reaction the catalyst is filtered off, the solution evaporated and the residue dissolved in 1 ml. of 1N methanolic hydrochloric acid then diluted with ether. The precipitated product is filtered, washed with ether and dried. Yield: 0.3 g. (93%) of the named pentapeptide ester hydrochloride; $R_f^4$ 0.55–0.60.

EXAMPLE 3

Preparation of
L-tyrosyl-D-methionyl-glycyl-L-phenylalanyl-L-norleucine 1.8 g. (3.7 mmoles) of Z-Gly-Phe-Nle-OMe (2nd step of Example 1) are dissolved in 30 ml. of methanol and hydrogenated in the presence of palladium catalyst. At the end of the reaction ($R_f^2$ 0.10–0.20) the catalyst is filtered off and the solution is evaporated. The residue is dissolved in 4 ml. of pyridine, then 1.56 g. (3.65 mmoles) of Boc-D-Met-OTCP (W. Broadbent et al.: J. Chem. Soc. 1967, 2632) are added and the solution allowed to stand for 5 hours. The reaction mixture is evaporated, the residue rubbed with a 1:1 mixture of ether and n-heptane, filtered, washed with said mixture and dried. The product obtained in this way ($R_f^2$ 0.70–0.75) is allowed to stand for 30 minutes with 5 ml. of 2N hydrochloric acid in ethyl acetate, then diluted with n-heptane, the precipitate filtered off, washed with n-heptane and dried in vacuo in the presence of potassium hydroxide. The obtained product (1.5 g.; $R_f^2$ 0.17–0.27) is suspended in a mixture of 2 ml. of pyridine and 2 ml. of dimethyl formamide. On adding 1.6 g. (3 mmoles) of Boc-Tyr-OTCP (D. A. Jones et al.: J. Org. Chem. 38, 2865/1973/) and 0.7 ml. (6 mmoles) of N-methylmorpholine, the mixture is stirred until the added substances are dissolved and then allowed to stand overnight. The reaction mixture is concentrated in vacuo and diluted with 30 ml. of ethyl acetate and 30 ml. of 0.5N sulphuric acid. The organic phase is washed with 0.5N sulphuric acid and with water, dried on sodium sulphate and evaporated. The residue is dissolved in 5 ml. of acetone and saponified with 1N sodium hydroxide in the presence of thymolphthalein as indicator. At the end of the reaction the solution is acidified with 0.5N sulphuric acid and shaken with ethyl acetate. The ethyl acetate phase is evaporated, then 10 ml. of 2N hydrochloric acid in ethyl acetate are poured onto the residue and the mixture is stirred. After half an hour the formed suspension is diluted with 10 ml. of water and the aqueous phase neutralized with N-methyl morpholine. On cooling, the precipitated crystals are filtered off, washed with some cold water and dried. Yield: 1.13 g. (60%) of the named pentapeptide; $R_f^3$ 0.3–0.4. Aminoacid analysis: Gly=1.0; Met=0.98; Nle=1.0; Tyr=0.96; Phe=1 (reference basis).

EXAMPLE 4

Preparation of
L-tyrosyl-D-alanyl-glycyl-L-phenylalanyl-L-isoleucine

1st step: Glycyl-L-phenylalanyl-L-isoleucine 1.95 g. (7 mmoles) of H-Phe-Ile-OH (J. T. Hill and W. F. Dunn: J. Med. Chem. 12, 737/1969/) are suspended in 10 ml. of pyridine, then 0.98 ml. (7 mmoles) of triethylamine and 2.72 g. (7 mmoles) of Z-Gly-OTCP added. The mixture is stirred until the added substances are dissolved and then allowed to stand overnight. The reaction mixture is evaporated, the residue dissolved in 50 ml. of ethyl acetate and so much 0.5N sulphuric acid that the aqueous phase attains a pH value of 2–3. The organic phase is washed with water, then the N-benzyloxycarbonyl peptide present as a solute is extracted with 3×20 ml. of a 5% solution of sodium hydrogen carbonate. The combined sodium hydrogen carbonate extracts are acidified with 0.5N sulphuric acid, the precipitated peptide is extracted with ethyl acetate and the ethyl acetate solution is evaporated. The residue ($R_f^2$ 0.5–0.6) is dissolved in 60 ml. of methanol and hydrogenated in the presence of palladium as catalyst. At the end of the reaction the catalyst is filtered off, washed with acetic acid, the filtrate combined with the washing liquid and evaporated. On rubbing the residue with ether, it is filtered, washed with ether and dried in vacuo in the presence of potassium hydroxide. Yield: 1.87 g. (80%) of the named tripeptide; $R_f^4$ 0.35–0.45.

2nd step: D-Alanyl-glycyl-L-phenylalanyl-L-isoleucine 1.68 g. (5 mmoles) of H-Gly-Phe-Ile-OH (1st step of Example 4) are suspended in 5 ml. of pyridine, then 0.7 ml. (5 mmoles) of triethylamine and 2.02 g. (5 mmoles) of Z-D-Ala-OTCP are added, stirred until the added substances are dissolved, and allowed to stand overnight. The reaction mixture is processed in the way specified in the 1st step. The obtained residue on evaporation ($R_f^2$ 0.50–0.55) is dissolved in 50 ml. of 80% acetic acid and hydrogenated in the presence of palladium as catalyst. At the end of the reaction the catalyst is filtered off and washed with acetic acid. The acetic acid solutions are combined, evaporated, rubbed with ether, filtered, washed with ether and dried in vacuo in the presence of potassium hydroxide. Yield: 1.7 g. (84%) of the named tetrapeptide; $R_f^4$ 0.10–0.15.

3rd step: L-Tyrosyl-D-alanyl-glycyl-L-phenylalanyl-L-isoleucine 1.22 g. (3 mmoles) of H-D-Ala-Gly-Phe-Ile-OH (2nd step of Example 4) are dissolved in pyridine, then 0.42 ml. (3 mmoles) of triethylamine and 1.48 g. (3 mmoles) of Z-Tyr-OTCP added, stirred until the added substances are dissolved and allowed to stand overnight. The reaction mixture is processed in the way specified in the 1st step. The obtained residue on evaporation ($R_f^2$ 0.55–0.60) is dissolved in 50 ml. of 80% acetic acid and hydrogenated in the presence of palladium as catalyst. At the end of the reaction the catalyst is filtered off and washed with acetic acid. The acetic acid solutions are combined, evaporated, rubbed with ether, filtered, washed with ether and dried in vacuo in the presence of potassium hydroxide. Yield: 1.4 g. (80%) of the named pentapeptide; $R_f^3$ 0.08–0.12. Aminoacid analysis: Gly=1.0; Ala=1.0; Nle=1.02; Tyr=0.96; Phe=1 (reference basis).

EXAMPLE 5

Preparation of
L-tyrosyl-D-alanyl-glycyl-L-phenylalanyl-L-proline

1st step: Glycyl-L-phenylalanyl-L-proline 5.25 g. (20 mmoles) of H-Phe-Pro-OH (S. Bajusz and T. Lázár: Acta Chim. Acad. Sci. Hung. 48, 111 (1966)) are suspended in 20 ml. of pyridine, then 2.8 ml. (20 mmoles) of triethylamine and 7.77 g. (20 mmoles) of Z-Gly-OTCP added, stirred until the substances are dissolved and allowed to stand overnight. The reaction mixture is processed in the way specified in the 1st step of Example 4. The product obtained as residue on evaporation ($R_f^2$ 0.5–0.6) is dissolved in 100 ml. of methanol and hydrogenated in the presence of palladium as catalyst. At the end of the reaction the catalyst is filtered off, washed with methanol, then the methanolic solutions are combined and evaporated. The residue is crystallized with ether, filtered, washed with ether and dried. Yield: 5.43 g. (85%) of the named tripeptide; $R_f^4$ 0.31–0.38.

2nd step: D-Alanyl-glycyl-L-phenylalanyl-L-proline 3.2 g. (10 mmoles) of H-Gly-Phe-Pro-OH (1st step of Example 5) are suspended in 10 ml. of pyridine, then 1.4 ml. (10 mmoles) of triethylamine and 4.03 g. (10 mmoles) of Z-D-Ala-OTCP are added and stirred until the substances are dissolved, and allowed to stand overnight. The reaction mixture is processed in the way specified in the 1st step of Example 4. The obtained residue on evaporation ($R_f^3$ 0.42–0.52) is dissolved in 80 ml. of methanol and hydrogenated in the presence of palladium as catalyst. At the end of the reaction the catalyst is filtered off, washed with methanol, then the methanolic solutions are combined and evaporated. The residue is rubbed with ether, filtered, washed with ether and dried. Yield: 3.2 g. (82%) of the named tetrapeptide; $R_f^4$ 0.07–0.11.

3rd step: Benzyloxycarbonyl-L-tryosyl-D-alanyl-glycyl-L-phenylalanyl-L-proline 3.12 g. (8 mmoles) of H-D-Ala-Gly-Phe-Pro-OH (2nd step of Example 5) are suspended in 15 ml. of pyridine, then 1.12 ml. (8 mmoles) of triethylamine and 3.95 g. (8 mmoles) of Z-Tyr-OTCP are added and stirred until the substances are dissolved, and then allowed to stand overnight. The reaction mixture is processed in the way specified in the 1st step of Example 4. The product obtained as residue on evaporation is rubbed with ether, filtered, washed with ether and dried. Yield: 4.4 g. (80%) of the protected named pentapeptide; $R_f^3$ 0.3–0.4.

4th step: L-Tyrosyl-D-alanyl-glycyl-L-phenylalanyl-L-proline

The solution of 2.06 g. (3 mmoles) of Z-Tyr-D-Ala-Gly-Phe-Pro-OH (3rd step of Example 5) in a mixture of 40 ml. of methanol and 10 ml. of dimethyl formamide are hydrogenated in the presence of palladium as catalyst. At the end of the reaction the catalyst is filtered off, washed with a 1:1 mixture of methanol and dimethyl formamide, the combined solutions are evaporated, the residue is rubbed with ether, filtered, washed with ether, dried, redissolved in 4 ml. of ethanol and precipitated with ethyl acetate. The precipitate is filtered, washed with ethyl acetate and dried. Yield: 1.16 g. (70%) of the named pentapeptide; $R_f^4$ 0.3–0.4. Aminoacid analysis: Pro=1.02; Gly=1.0; Ala=0.98; Tyr=1.0; Phe=1 (reference basis).

EXAMPLE 6

Preparation of
L-tyrosyl-D-alanyl-glycyl-L-phenylalanyl-L-proline ethylamide 0.7 g. (1 mmoles) of Z-Tyr-D-Ala-Gly-Phe-Pro-OH (3rd step of Example 5) are dissolved in 2 ml. of dimethyl formamide, then 0.1 g. (1.24 mmoles) of ethylamine hydrochloride, 0.17 ml. (1.24 mmoles) of triethylamine and 0.21 g. (1 mmole) of dicyclohexyl-carbodiimide are added. The reaction mixture is allowed to stand for one day, filtered and diluted with 30 ml. of ethyl acetate. The solution is washed with 0.5N sulphuric acid, water, 5% solution of sodium hydrogen carbonate and water, then dried and evaporated. The residue on evaporation ($R_f^2$ 0.80–0.85) is dissolved in 30 ml. of methanol and hydrogenated in the presence of palladium as catalyst. At the end of the reaction the catalyst is filtered off, the solution evaporated, rubbed with ether, filtered, washed with ether and dried. Yield: 0.43 g. (75%) of the named pentapeptide; $R_f^4$ 0.34–0.44.

EXAMPLE 7

Preparation of
L-tyrosyl-D-methionyl-glycyl-L-phenylalanyl-L-proline hydrochloride 0.96 g. (3 mmoles) of H-Gly-Phe-Pro-OH (1st step of Example 5) are suspended in 5 ml. of pyridine, then 0.42 ml. (3 mmoles) of triethylamine and 1.27 ml (3 mmoles) of Boc-D-Met-OTCP added, stirred until the substances are dissolved, and allowed to stand overnight. The reaction mixture is processed in the way specified in the 1st step of Example 4. Then 10 ml. of 2N hydrochloric acid in ethyl acetate are poured onto the substance obtained as residue on evaporation ($R_f^2$ 0.30–0.35) and the mixture is stirred. After half an hour the reaction mixture is diluted with n-heptane, filtered, washed with n-heptane and dried in vacuo in the presence of potassium hydroxide. The product obtained in this way ($R_f^4$ 0.16–0.24) is suspended in 5 ml. of pyridine, then 0.84 ml. (6 mmoles) of triethylamine and 1.32 g. (2.5 mmoles) of Boc-Tyr-OPCP are added, stirred until the substances are dissolved, and allowed to stand overnight. The reaction mixture is processed in the way specified in the 1st step of Example 4. The residue on evaporation is dissolved in 10 ml. of 2N hydrochloric acid in ethyl acetate, stirred for half an hour, diluted with 10 ml. of ethyl acetate, filtered, washed with ethyl acetate and dried. Yield: 1.14 g. (70%) of the named pentapeptide hydrochloride; $R_f^4$ 0.35–0.45. Aminoacid analysis: Pro=0.98; Gly=1.0; Met=0.95; Tyr=1.0; Phe=1 (reference basis).

EXAMPLE 8

Preparation of
L-tyrosyl-D-norleucyl-glycyl-L-phenylalanyl-L-proline hydrochloride On starting with 0.96 g. (3 mmoles) of H-Gly-Phe-Pro-OH (1st step of Example 5), the procedure specified in Example 7 is followed with the difference that instead of 1.27 g. of Boc-D-Met-OTCP, 1.06 g. (3 mmoles) of Boc-D-Nle-ONP (R. Rocchi et al.: J. Am. Chem. Soc. 91, 492 (1969)) are applied. Yield: 1.18 g. (75%) of the named pentapeptide hydrochloride; $R_f^4$ 0.35–0.45. Aminoacid analysis: Pro=1.0; Gly=1.0; Nle=1.05; Tyr=0.98; Phe=1 (reference basis).

EXAMPLE 9

Preparation of
L-tyrosyl-D-methionyl-glycyl-L-phenylalanyl-L-proline ethylamide

1st step: Glycyl-L-phenylalanyl-L-proline ethylamide oxalate 3.7 g. (13 mmoles) of Pro-NH-Et (S. Shinagawa and M. Fujino: Chem. Pharm. Bull. 23, 229/1975/) are dissolved in 50 ml. of methanol and hydrogenated in the presence of palladium catalyst. At the end of the reaction ($R_f^3$ 0.2–0.3) the catalyst is filtered off, washed with methanol, the methanolic solutions are evaporated, and the residue is dissolved in 10 ml. of dimethyl formamide. On adding 3.9 g. (13 mmoles) of Z-Phe-OH, 1.75 g. (13 mmoles) of 1-hydroxybenztriazole and 2.7 g. (13 mmoles) of dicyclohexylcarbodiimide the reaction mixture is allowed to stand overnight and then evaporated. The residue is dissolved in 50 ml. of ethyl acetate and consecutively washed with a 5% solution of sodium hydrogen carbonate, water, 0.5N sulphuric acid and water again. The organic phase is dried on sodium sulphate and evaporated. The obtained product ($R_f^2$ 0.63–0.68) is dissolved in 50 ml. of methanol and hydrogenated in the presence of palladium as catalyst. The catalyst is filtered off and the methanolic solution evaporated. The residue ($R_f^3$ 0.1–0.2) is dissolved in 10 ml. of pyridine, then 2.09 g. (10 mmoles) of Z-Gly-OTCP are added. The reaction mixture is allowed to stand overnight, then evaporated. The residue on evaporation is dissolved in 50 ml. of ethyl acetate, washed with 0.5N sulphuric acid, then the organic phase is dried on sodium sulphate and evaporated. The residue is dissolved in 50 ml. of methanol and hydrogenated in the presence of palladium as catalyst. At the end of the reaction the catalyst is filtered off, and the solution is evaporated. The residue on evaporation is dissolved in a mixture of 2 ml. of ethanol and 2 ml. of ethyl acetate, then 0.9 g. (10 mmoles) of oxalic acid are added and the mixture is diluted with 50 ml. of ethyl acetate. The precipitated product is filtered, washed with ethyl acetate and dried. Yield: 2.7 g. (62%) of the named tripeptide ethylamide oxalate; m.p. 98°–100°; $R_f^4$ 0.4–0.5.

2nd step: L-Tyrosyl-D-methionyl-glycyl-L-phenylalanyl-L-proline ethylamide 0.9 g. (2 mmoles) of the tripeptide ethylamide oxalate (1st step of Example 9) are dissolved in 3 ml. of pyridine, then 0.86 g. (2 mmoles) of Boc-Met-OTCP and 0.56 ml. (4 mmoles) of triethylamine are added. The reaction mixture is allowed to stand overnight, then evaporated, dissolved in 30 ml. of ethyl acetate, washed with 0.5N sulphuric acid, dried on sodium sulphate and evaporated. The residue ($R_f^2$ 0.80–0.85) is allowed to stand with 10 ml. of 3N hydrochloric acid in ethyl acetate, after half an hour diluted with 30 ml. of n-heptane, the precipitate formed is filtered, washed with n-heptane and dried in vacuo in the presence of potassium hydroxide. The obtained product is dissolved in 5 ml. of pyridine, and 1.06 g. (2 mmoles) of Boc-Tyr-OPCP and 0.56 ml. (4 mmoles) of triethylamine are added. The reaction mixture is allowed to stand overnight, then evaporated, dissolved in 50 ml. of ethyl acetate, washed with 0.5N sulphuric acid, dried on sodium sulphate and evaporated. The residue ($R_f^2$ 0.85–0.90) is dissolved in 3 ml. of trifluoroacetic acid and allowed to stand for half an hour. The solution containing a precipitate is evaporated and the residue rubbed with a 1:1 mixture of ethyl acetate and benzene. The obtained product is dissolved in a mixture of 5 ml. of 10% sodium carbonate solution and 50 ml. ethyl acetate. The aqueous phase is shaken with 3×10 ml. of ethyl acetate, the combined ethyl acetate solutions dried on sodium sulphate and evaporated. The residue on evaporation is rubbed with a 1:1 mixture of n-heptane and ethyl acetate, filtered, washed with this mixture and then with n-heptane, and dried. Yield: 1.02 g. (80%) of the named pentapeptide ethylamide; $R_f^4$ 0.45–0.55. Aminoacid analysis: Pro=1.0; Gly=1.0; Met=0.98; Tyr=1.02; Phe=1 (reference basis).

EXAMPLE 10

Preparation of
L-tyrosyl-D-methionyl-glycyl-L-phenylalanyl-L-proline amide 0.96 g. (3 mmoles) of H-Gly-Phe-Pro-OH (1st step of Example 5) are suspended in 5 ml. of pyridine, then 0.42 ml. (3 mmoles) of triethylamine and 1.27 g. (3 mmoles) of Boc-D-Met-OTCP are added and stirred until the substances are dissolved. After allowing the reaction mixture to stand overnight, it is processed in the way specified in the 1st step of Example 4. On pouring 10 ml. of 2N hydrochloric acid in ethyl acetate onto the obtained residue on evaporation ($R_f^2$ 0.30–0.35), the mixture is stirred. After half an hour the reaction mixture is diluted with n-heptane, filtered, washed with n-heptane and dried in vacuo in the presence of potassium hydroxide. The product obtained in this way ($R_f^4$ 0.16–0.24) is suspended in 5 ml. of pyridine, then 0.84 g. (6 mmoles) of triethylamine and 1.32 g. (2.5 mmoles) of Boc-Tyr-OPCP are added and stirred until the substances are dissolved. After allowing the reaction mixture to stand overnight, it is processed in the way specified in the 1st step of Example 4. The residue on evaporation is rubbed with h-heptane, filtered, washed with n-heptane and dried. The obtained Boc-Tyr-D-Met-Gly-Phe-Pro-OH ($R_f^4$ 0.60–0.66) is dissolved in 5 ml. of dimethyl formamide, then 0.52 g. (2.5 mmoles) of dicyclohexyl-carbodiimide and 0.4 g. (2.5 mmoles) of 1-hydroxybenzotriazole ammonium salt are added. (The latter is prepared as follows: a solution of 1-hydroxy-benzotriazole in concentrated aqueous ammonium hydroxide (0.5 g/ml.) is diluted with acetone, then the precipitated crystals are filtered, washed with acetone and dried.) The reaction mixture for amidation is allowed to stand overnight, filtered, evaporated, the residue on evaporation dissolved in methylene chloride, washed with a 5% solution of sodium hydrogen carbonate, dried on sodium sulphate and evaporated. The residue on evaporation ($R_f^1$ 0.53–0.58) is dissolved in 10 ml. of trifluoroacetic acid, allowed to stand for 30 minutes at room temperature, then evaporated and the residue ($R_f^4$ 0.50–0.60) dried in vacuo in the presence of potassium hydroxide. The product obtained in this way is dissolved in 30–40 ml. of a 3:1 mixture of chloroform and n-butanol, and 5–7 ml. of water. The aqueous phase is neutralized with solid sodium hydrogen carbonate, extracted with the aforementioned mixture of chloroform and n-butanol, then the combined organic phases are evaporated and the residue is rubbed with n-heptane. Yield: 1.25 g. of the named product which is, according to our investigations carried out by the methods of D'Amour and Smith (J. Pharm. Ther. 72, 74 (1941)) and Chermat and Simon (J. Pharmacol. (Paris) 6, 489 (1975)), in vivo about fifty-times more active than morphine. Aminoacid analysis: Pro=1.0; Gly=1.0; Met=1.0; Tyr=0.98; Phe=1 (reference basis).

EXAMPLE 11

Preparation of L-tyrosyl-D-alanyl-glycyl-L-phenylalanyl-L-proline amide 2.06 g. (3 mmoles) of Z-Tyr-D-Ala-Gly-Phe-Pro-OH (3rd step of Example 5) are dissolved in 5 ml. of dimethyl formamide, then 0.46 g. (3 mmoles) of 1-hydroxybenzotriazole ammonium salt and 0.62 g. (3 mmoles) of dicyclohexyl-carbodiimide are added. The reaction mixture is allowed to stand overnight, then filtered and evaporated. The residue on evaporation is dissolved in methylene chloride, washed with a 5% solution of sodium hydrogen carbonate, dried on sodium sulphate and evaporated. The residue on evaporation ($R_f^2$ 0.60–0.65) is dissolved in 40–50 ml. of methanol and hydrogenated in the presence of palladium as catalyst. At the end of the reaction ($R_f^4$ 0.33–0.38) the catalyst is filtered off, the solution evaporated and the residue rubbed with ether. Yield: 1.2 g. (70%) of the named product. Aminoacid analysis: Pro=1.0; Gly=1.0; Ala=1.0; Tyr=0.97; Phe=1 (reference basis).

What we claim is:

1. L-tyrosyl-D-methionyl-glycyl-L-phenylalanyl-L-proline amide.

* * * * *